(12) United States Patent
Dolla et al.

(10) Patent No.: US 10,544,887 B2
(45) Date of Patent: Jan. 28, 2020

(54) TUBE

(71) Applicant: RAUMEDIC AG, Münchberg (DE)

(72) Inventors: Andreas Dolla, Hof (DE); Jörg Bruns, Hof (DE)

(73) Assignee: RAUMEDIC AG, Munich (DE)

( * ) Notice: Subject to any disclaimer, the term of this patent is extended or adjusted under 35 U.S.C. 154(b) by 16 days.

(21) Appl. No.: 15/758,068

(22) PCT Filed: Aug. 31, 2016

(86) PCT No.: PCT/EP2016/070506
§ 371 (c)(1),
(2) Date: Mar. 7, 2018

(87) PCT Pub. No.: WO2017/042074
PCT Pub. Date: Mar. 16, 2017

(65) Prior Publication Data
US 2018/0252341 A1  Sep. 6, 2018

(30) Foreign Application Priority Data
Sep. 7, 2015  (DE) .......................... 10 2015 217 061

(51) Int. Cl.
| F16L 9/18 | (2006.01) |
| F16L 11/22 | (2006.01) |
| A61B 1/012 | (2006.01) |
| F16L 11/08 | (2006.01) |
| B29C 48/11 | (2019.01) |
| B29C 48/21 | (2019.01) |
| B29L 31/00 | (2006.01) |

(52) U.S. Cl.
CPC .............. *F16L 11/22* (2013.01); *A61B 1/012* (2013.01); *F16L 11/08* (2013.01); *B29C 48/11* (2019.02); *B29C 48/21* (2019.02); *B29L 2031/7546* (2013.01)

(58) Field of Classification Search
CPC ....... F16L 11/22; F16L 11/08; A61M 25/0133
USPC .......................... 138/115–117; 604/43, 95.04
See application file for complete search history.

(56) References Cited

U.S. PATENT DOCUMENTS

| 3,517,110 A | * | 6/1970 | Morgan | ................ E21B 17/012 114/230.13 |
| 3,526,086 A | * | 9/1970 | Morgan | .................... F16L 9/18 138/111 |
| 4,399,319 A | * | 8/1983 | Zinn | ..................... F16L 11/127 174/47 |
| 5,713,851 A | * | 2/1998 | Boudewijn | ....... A61M 25/0009 604/264 |

(Continued)

FOREIGN PATENT DOCUMENTS

| DE | 69422556 T2 | 8/2000 |
| DE | 69732864 T2 | 4/2006 |

(Continued)

*Primary Examiner* — Patrick F Brinson
(74) *Attorney, Agent, or Firm* — Browdy and Neimark, PLLC

(57) ABSTRACT

A tube has a tube body. In the tube body, at least one high-pressure lumen and at least one low-pressure lumen are embedded. The at least one high-pressure lumen and the at least one low-pressure lumen are embedded in the tube body as a bundle configured as a lumen bundle. As a result, a tube body is obtained that is flexibly adaptable to various conditions of use.

11 Claims, 2 Drawing Sheets

(56) References Cited

U.S. PATENT DOCUMENTS

| | | | | |
|---|---|---|---|---|
| 6,311,730 | B2* | 11/2001 | Penza | F16L 11/20 |
| | | | | 138/114 |
| 8,202,265 | B2 | 6/2012 | Boulais | |
| 2006/0151040 | A1* | 7/2006 | Olsen | F16L 11/081 |
| | | | | 138/115 |
| 2007/0161970 | A1 | 7/2007 | Spohn et al. | |
| 2007/0276324 | A1* | 11/2007 | Laduca | A61M 25/008 |
| | | | | 604/95.04 |
| 2008/0058720 | A1 | 3/2008 | Spohn et al. | |

FOREIGN PATENT DOCUMENTS

| | | |
|---|---|---|
| EP | 0637453 A1 | 2/1995 |
| WO | 9824501 A1 | 6/1998 |
| WO | 2009120871 A2 | 10/2009 |
| WO | 2013023213 A1 | 2/2013 |

* cited by examiner

TUBE

CROSS-REFERENCE TO RELATED APPLICATIONS

This application claims the priority of German Patent Application Serial No. DE 10 2015 217 061.6, filed on Sep. 7, 2015, pursuant to 35 U.S.C. 119(a)-(d), the content of which is incorporated herein by reference in its entirety as if fully set forth herein.

FIELD

The invention relates to a tube, in particular for a medical application.

BACKGROUND

A tube of this type is known through prior public use. Document DE 694 22 556 T2 describes a method for the production of a catheter comprising at least one high-pressure lumen and a catheter. Document DE 697 32 864 T2 describes a multi-lumen access device configured to create an access to the human body. Document U.S. Pat. No. 8,202,265 B2 describes a multi-lumen assembly for use in endoscopes.

SUMMARY

An object of the present invention is to provide a tube of the aforementioned type that is flexibly adaptable to various conditions of use.

This object is achieved according to the invention by a tube comprising a tube body of a polymer in which at least one high-pressure (HP) lumen and at least one low-pressure (LP) lumen are embedded, wherein the at least one HP lumen and the at least one LP lumen are embedded in the tube body as a bundle configured as a lumen bundle.

The at least one high-pressure lumen is hereinafter also referred to as HP lumen and is resistant to pressures above a pressure of 80 bar and may be resistant to pressures of up to 130 bar, for example. The at least one low-pressure lumen, which is hereinafter also referred to as LP lumen, is resistant to pressures of up to 30 bar.

The at least one HP lumen and the at least one LP lumen may be extruded, and afterwards assembled, in separate sections of an extrusion tool. The at least one LP lumen can be used as a gas return lumen. The following materials are suitable for use as the tube body material: thermoplastic polyurethane (TPU), polyether block amide (PEBA), soft (i.e. having a Shore hardness of "A", for example) thermoplastic elastomer (TPE) on a styrol/ethene butene (SEBS) or polyvinylchloride (PVC) basis. The tube may be used as an endoscopic tube, for example. The lumen bundle of the at least one HP lumen and of the at least one LP lumen and the embedding of the lumen bundle in the polymer tube body increases the stability of the tube. This embedding ensures that a position of the various lumina is defined exactly across the entire tube cross-section. A bending stiffness of the entire tube can be influenced additionally by selecting an appropriate embedding material. Contrary to other multilumen tubes, at least one lumen is not formed directly in the material of the tube body but is configured as a lumen having its own lumen wall. This may be the case in particular for the at least one high-pressure lumen. The low-pressure lumina may either be configured as recesses in the polymer tube body material directly or they may be configured as lumina having their own respective individual lumen walls. Individual lumen walls of the respective lumina, which are in turn embedded in the polymer tube body material, simplify the production of the tube having a plurality of lumina. Tubes pre-fabricated accordingly in such a way as to correspond to the individual lumina may then, in a subsequent step, be surrounded by the polymer tube body material so as to be embedded therein.

A sheathing, which is embedded in the tube body as well and is provided such as to surround the lumen bundle, may increase the stability of the entire tube even more. Having provided the sheathing, consisting of a polymer or metal net, for example, it is then possible to provide an additional outer tube body coating, consisting in particular of a polymer. This may in particular be done by means of a coextrusion process. The sheathing may further fulfill the purpose of reinforcement.

Materials used for the sheathing such as a polymer material or metal wires have proven well in practical application. The polymer material may be polyethylene terephthalate (PET) or polyamide (PA).

A sheathing having a signal transmission function provides an extended range of potential applications of the tube. It is possible to provide a unidirectional or a bidirectional signal transmission. An assembly including the entire tube may be provided with at least one signal generator, for example a sensor, and with at least one signal receiver, for example an external evaluation unit such as a computer.

An HP lumen configured as exactly one HP lumen extending centrally through the tube may be configured as a reinforced monotube. A monotube tube material of the HP lumen may differ from the material of the tube body. A reinforcement of the HP lumen may be configured as a stainless steel reinforcement.

Providing two LP lumina ensure greater flexibility of using the tube. It is conceivable as well for three, four or even more LP lumina to be embedded in the tube body. The LP lumina may be arranged in a radially outer region of the tube cross-section.

Providing at least two LP lumina extending in a radially inner region of the tube cross-section ensure greater flexibility of using the tube.

The tube body and the LP lumina may be made of a soft and flexible material.

At least one metal strand embedded in the tube body allows a signal transmission or, alternatively, an absorption of tensile forces or—when designed as a Bowden cable— allows a tube layout to be defined in a controlled manner. There may be two, three, four or even more metal strands embedded in the tube body. The metal strands may be arranged in a radially outer region of the tube cross-section. Alternatively, a metal fiber, a polymer fiber or an optical fiber may be embedded the tube body. Fibers of this type may be used for signal transmission and/or for guiding light.

A working lumen embedded in the tube body may be used to guide a separate Bowden cable, a separate tube or a separate probe. The working lumen also allows metal, polymer or optical fibers to be guided. Fibers of this type may be used for signal transmission and/or for guiding light.

A monotube configuration of at least one of the lumina, wherein the tube material of which differs from the material of the tube body, increases the flexibility of the tube configuration.

The low pressure lumen and/or the working lumen may be made of the following tube materials: polymer having a Shore hardness in the "A" range, for example thermoplastic polyurethane (TPU), polyether block amide (PEBA), soft thermoplastic elastomer (TPA) on a styrol/ethene butene (SEBS) basis.

The HP lumen may be made of the following tube materials: polyamide (PA), polytetrafluoroethylene (PTFE), tetrafluoroethylene/hexafluoropropylene (FPE), polyether ether ketone (PEEK), polyetherimide (PEI), fluorinated polymer or a metal such as stainless steel.

A reinforcement of at least one of the lumina increases the stability of said lumen, in particular the pressure/rupture resistance thereof. Suitable materials for the reinforcement and/or the sheathing of the lumen bundle include: polyethylene terephthalate (PET), polyamide (PA) or metal wires. The reinforcement may be made of monofilaments and/or multifilaments. The reinforcement and/or the sheathing may have a signal transmitting function. A reinforcement of this type increases the bending resistance of the tube.

Exemplary embodiments of the invention will hereinafter be explained in more detail, taken in conjunction with the drawing.

DETAILED DESCRIPTION

Figure 1:
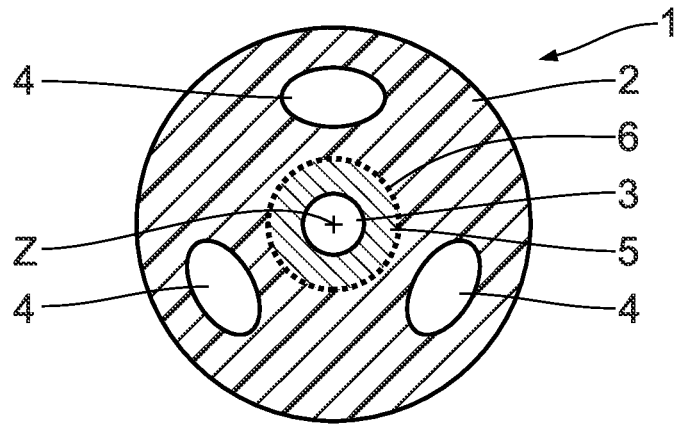
FIG. 1 shows a cross-sectional view of a multilumen tube, which may be used as an endoscopic tube, comprising a high-pressure lumen extending centrally through the tube and three low-pressure lumina arranged in a radially outer region of the tube cross-section.

A multilumen tube 1, which is shown in a cross-sectional view in FIG. 1, can be used as a medical tube, and in particular as an endoscopic tube. The tube 1 has a tube body 2 with one high-pressure lumen (HP lumen) 3 and three low-pressure lumina (LP lumina) 4 being embedded therein. The HP lumen 3 may be used as a high-pressure resistant feed line for a medium, and may be resistant to high pressures of up to 130 bar, for example. The LP lumina 4 may be used as low-pressure resistant gas return lines.

The tube body 2 is made of a polymer having a Shore hardness in the range of "A", for example a thermoplastic polyurethane (TPU), a polyether block amide (PEBA), a soft thermoplastic elastomer (TPE) on a styrol/ethene butene (SEBS) basis or a soft polyvinylchloride (PVC).

The HP lumen 3 has a round cross-section.

The HP lumen 3 extends centrally through the tube 1. The HD lumen 3 is configured as a reinforced monotube. A lumen wall 5 of the HP lumen 3 is made of polyamide (PA), of polytetrafluoroethylene (PTFE), of tetrafluoroethylene/hexafluoropropylene (FPE), of polyether ether ketone (PEEK), of polyetherimide (PEI), of a fluorinated polymer or, alternatively, of a metal such as stainless steel. In other words, the monotube material of the HP lumen 3 differs from the material of the tube body 2.

The lumen wall 5 is surrounded by a stainless steel reinforcement 6 arranged in the region of a boundary surface between the lumen wall 5 and the surrounding tube body 2. The stainless steel reinforcement 6 is made of 12 reinforcing fibers or wires surrounding the lumen wall 5. Alternatively, the stainless steel reinforcement 6 may also be made of 16, of 24 or of 32 reinforcing fibers or wires surrounding the lumen wall 5. The stainless steel reinforcement 6 may be made of wire, of monofilaments and/or of multifilaments. The filaments or the wire may have a diameter in the range of 0.04 to 0.08 mm.

The three LP lumina 4 are arranged in a radially outer region of the tube cross-section of the multilumen tube 1.

The LP lumina 4 each have an elliptical cross-section. A semi-major ellipse axis of said elliptical cross-section is tangential to the center of the cross-section of the tube 1.

The three LP lumina 4 are arranged about the center of the tube 1 in such a way as to be distributed equally. The three LP lumina 4 each have identical cross-sectional areas. A lumen wall of the LP lumina 4 is formed seamlessly of the material of the tube body 2.

Another embodiment of a multilumen tube 7 will hereinafter be explained by means of FIG. 2. Components and functions, which have already been described above with reference to FIG. 1, carry the same reference numerals and are not discussed in detail again.

The multilumen tube 7 has two HP lumina 3a and 3b extending in a radially inner region of the tube cross-section and two LP lumina 4. The HP lumina 3a and 3b have a smaller distance from a cross-sectional center Z of the tube body 2 than the two LP lumina 4.

Both the two HP lumina 3a, 3b and the two LP lumina 4 are arranged opposite one another in relation to said cross-sectional center Z.

Another embodiment of a multilumen tube 8 will hereinafter be explained by means of FIG. 3. Components and functions, which have already been described above with reference to FIGS. 1 and 2, and with particular reference to FIG. 1, carry the same reference numerals and are not discussed in detail again.

In terms of the arrangement of the high-pressure lumen 3 and the three low-pressure lumina 4, the multilumen tube 8 is identical to the multilumen tube 1. In addition thereto, the multilumen tube 8 is provided with three metal strands 9 configured as stainless steel strands, which are embedded in the tube body 2. These metal strands 9 may be used to absorb tensile forces acting on the tube 8 or they may each be used as a Bowden cable to influence a layout of the tube 8.

The three metal strands 9 are arranged in a radially outer region of the tube cross-section and have approximately the same distance from the cross-sectional center Z as the LP lumina 4. The three metal strands 9 are equally distributed about the cross-sectional center Z as well. This arrangement is such that one respective metal strand 9 is arranged at the same distance from two adjacent LP lumina 4.

Another embodiment of a multilumen tube 10 will hereinafter be explained by means of FIG. 4. Components and functions, which have already been described above with reference to FIGS. 1 to 3, and with particular reference to FIG. 2, carry the same reference numerals and are not discussed in detail again.

Figure 2:
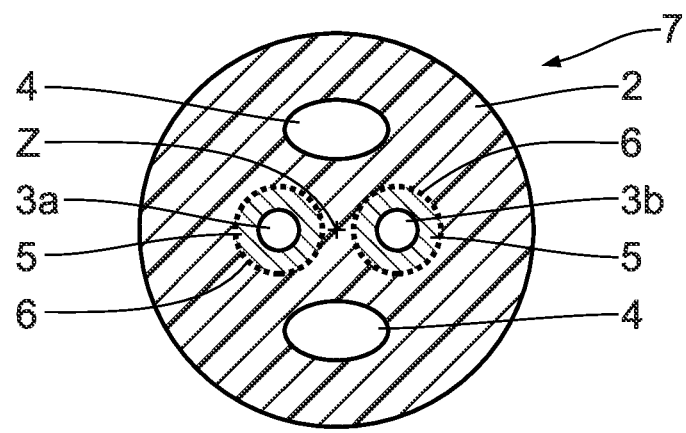
FIG. 2 shows a view, similar to FIG. 1, of another embodiment of a multilumen tube comprising two high-pressure lumina extending in a radially inner region of the tube cross-section and two low-pressure lumina extending in a radially outer region of the tube cross-section.
Figure 3:
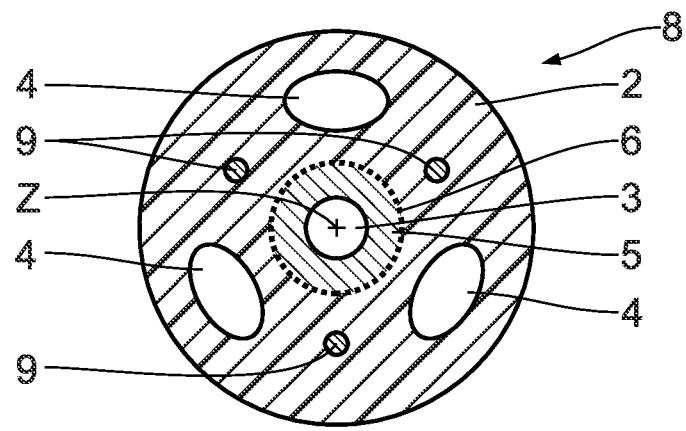
FIG. 3 shows a view, similar to FIG. 1, of another embodiment of a multilumen tube with a lumen arrangement as shown in FIG. 1 and three additional metal strands embedded in the radially outer region of the tube cross-section.

The arrangement of the HP lumina 3a, 3b and of the LP lumina 4 is the same in the multilumen tube 10 as in the multilumen tube 7 as shown in FIG. 2. The multilumen tube 10 has an additional four metal strands 9. Said additional metal strands 9 are arranged in the four quadrants of a coordinate system defined by the arrangement coordinates x of the two HP lumina 3a and 3b and y of the two LP lumina 4. The cross-sectional center Z lies in the origin of this xyz coordinate system.

Figure 4:
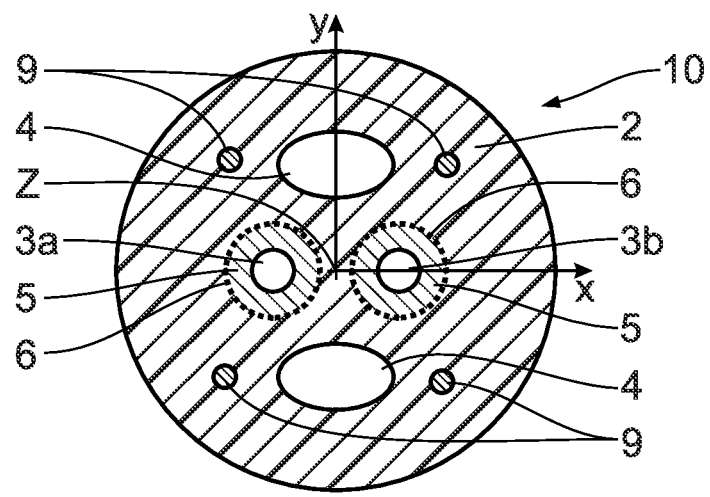
FIG. 4 shows a view, similar to FIG. 2, of another embodiment of a multilumen tube with a lumen arrangement as shown in FIG. 2 and three additional metal strands embedded in the radially outer region of the tube cross-section.

As shown in FIG. 4, the four metal strands 9 are arranged such as to be equally distributed about the cross-sectional center Z when seen in the circumferential direction.

Figure 5:
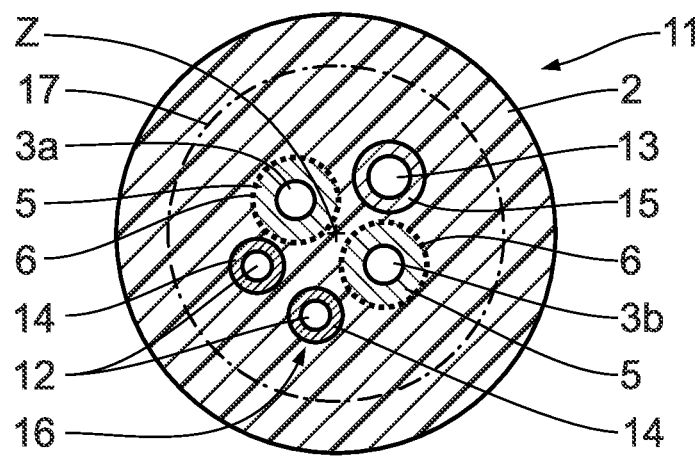
FIG. 5 shows a view, similar to FIG. 1, of another embodiment of a multilumen tube, wherein two high-pressure lumina, two low-pressure lumina and one working lumen are embedded in the tube body as a bundle configured as a lumen bundle, and the lumen bundle is surrounded by a sheathing, which is embedded in the tube body as well.

Another embodiment of a multilumen tube 11 will hereinafter be explained by means of FIG. 5. Components and functions, which have already been described above with reference to FIGS. 1 to 4, and with particular reference to FIG. 3, carry the same reference numerals and are not discussed in detail again.

The multilumen tube 11 has two HP lumina 3a and 3b, two LP lumina 12 and one working lumen 13. Contrary to the LP lumina 4, the LP lumina 12 of the multilumen tube 11 are configured as monotubes the lumen walls 14 of which are made of a material that differs from the tube material of the tube body 2. The tube material of these lumen walls 14 of the LP lumina 12 may be made of one of the materials specified above in connection with the material of the tube body 2. The same applies to a material of a lumen wall 15 of the working lumen 13.

The working lumen 13 may also be used to guide a Bowden cable introduced therein of a separated tube introduced therein or a probe introduced therein. The working lumen may also used to guide metal, polymer or optical fibers, which may be used for signal transmission, for example.

The lumina 3a, 3b, 12 and 13 of the multilumen tube 11 are embedded in the tube body 2 as a bundle configured as a lumen bundle 16. The lumen bundle 16 is surrounded by a sheathing 17 embedded in the tube body 2 as well.

The reinforcement 6 and/or the sheathing 17 may be made of a polymer material such as polyethylene terephthalate (PET), of a polyamide (PA) or of metal wires. The reinforcement 6 and/or the sheathing 17 may have a signal transmitting function.

Figure 6:
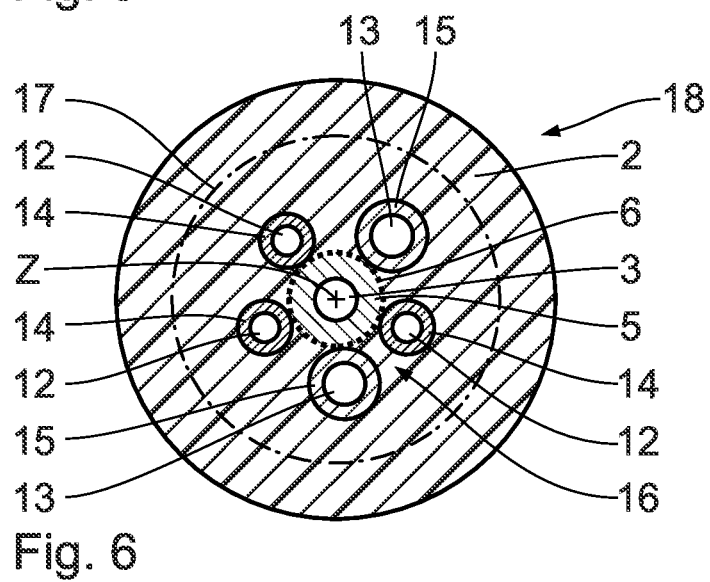
FIG. 6 shows a view, similar to FIG. 5, of another embodiment of a multilumen tube comprising one central high-pressure lumen, two low-pressure lumina and two working lumina, which are configured as a bundled and sheathed lumen bundle as well.

Another embodiment of a multilumen tube 18 will hereinafter be explained by means of FIG. 6. Components and functions, which have already been described above with reference to FIGS. 1 to 5, and with particular reference to FIG. 4, carry the same reference numerals and are not discussed in detail again.

In the multilumen tube 18, the lumen bundle 16 comprises a central HP lumen 3, three LP lumina 12 and two working lumina 13.

The at least one LP lumen may also be used as a working duct or a guide duct. In the at least one LP lumen, a probe and/or a tool may be guided. Alternatively or additionally, the at least one LP lumen may also be used as a flushing duct or a liquid duct.

The invention claimed is:

1. A tube comprising a tube body of a polymer in which at least one high-pressure (HP) lumen and at least one low-pressure (LP) lumen are embedded, wherein the at least one HP lumen and the at least one LP lumen are embedded in the tube body as a bundle configured as a lumen bundle.

2. The tube according to claim 1, wherein the lumen bundle is surrounded by a sheathing embedded in the tube body as well.

3. The tube according to claim 2, wherein the sheathing is made of one of the group comprising a polymer material and metal wires.

4. The tube according to claim 2, wherein the sheathing is configured for signal transmission.

5. The tube according to claim 1, comprising exactly one HP lumen extending centrally through the tube.

6. The tube according to claim 1, comprising at least two LP lumina.

7. The tube according to claim 1, comprising at least two HP lumina extending in a radially inner region of the tube cross-section.

8. The tube according to claim 1, comprising at least one metal strand embedded in the tube body.

9. The tube according to claim 1, comprising at least one working lumen embedded in the tube body.

10. The tube according to claim 1, wherein at least one of the lumina is configured as a monotube the tube material of which differs from the material of the tube body.

11. The tube according to claim 1, wherein at least one of the lumina is provided with a reinforcement.

* * * * *